United States Patent
Brown et al.

(10) Patent No.: US 10,441,706 B2
(45) Date of Patent: Oct. 15, 2019

(54) SYSTEM AND METHOD FOR IMPROVED FLUID FLOW CONTROL WITHIN A FLUID CIRCUIT CASSETTE

(71) Applicant: Fenwal, Inc., Lake Zurich, IL (US)

(72) Inventors: David S. Brown, Lake Barrington, IL (US); Sukhraaj Basati, Schaumburg, IL (US)

(73) Assignee: Fenwal, Inc., Lake Zurich, IL (US)

( * ) Notice: Subject to any disclaimer, the term of this patent is extended or adjusted under 35 U.S.C. 154(b) by 289 days.

(21) Appl. No.: 15/436,369

(22) Filed: Feb. 17, 2017

(65) Prior Publication Data
US 2017/0239403 A1 Aug. 24, 2017

Related U.S. Application Data

(60) Provisional application No. 62/297,549, filed on Feb. 19, 2016.

(51) Int. Cl.
*A61M 1/36* (2006.01)
*A61M 1/02* (2006.01)
*A61M 1/26* (2006.01)

(52) U.S. Cl.
CPC ............ *A61M 1/367* (2013.01); *A61M 1/025* (2013.01); *A61M 1/029* (2013.01); *A61M 1/0272* (2013.01); *A61M 1/265* (2014.02); *A61M 1/36* (2013.01); *A61M 1/3672* (2013.01); *A61M 2202/0439* (2013.01);
(Continued)

(58) Field of Classification Search
CPC ...... A61M 1/36; A61M 1/367; A61M 1/3672; A61M 2205/12; A61M 2205/123; A61M 2205/128; A61M 2205/3337
See application file for complete search history.

(56) References Cited

U.S. PATENT DOCUMENTS 5,868,696 A 2/1999 Giesler et al.
7,789,245 B2 9/2010 Westberg et al.

FOREIGN PATENT DOCUMENTS

EP 3088019 A1 11/2016
WO 2012141697 A1 10/2012
(Continued)

OTHER PUBLICATIONS

European Search Report for application No. 17156063.4, dated Jul. 11, 2017, 8 pages.

*Primary Examiner* — John Kim
(74) *Attorney, Agent, or Firm* — Cook Alex Ltd.

(57) ABSTRACT

A fluid processing system for controlling fluid flow comprises a cassette having a defined passageway on a first side. The first side includes flexible sheeting disposed over the passageway. The system comprises a durable processing device configured to engage the first side of the cassette, the durable processing device comprising a valve actuator configured to engage the flexible sheeting at a valve location along the passageway. The system comprises a first pump configured to draw fluid away from the valve location along the passageway. The first pump is disposed downstream of the valve location. The system comprises a second pump configured to pump fluid towards the valve location along the defined passageway. The second pump is disposed upstream of the valve location. The first and second pumps are configured to operate in concert and configured to provide pressure to prevent collapsing of the flexible sheeting against the passageway during operation.

20 Claims, 10 Drawing Sheets

(52) U.S. Cl.
CPC ............... *A61M 2205/128* (2013.01); *A61M 2205/3337* (2013.01); *A61M 2230/207* (2013.01)

(56) References Cited

FOREIGN PATENT DOCUMENTS

| | | |
|---|---|---|
| WO | 2014/039086 A1 | 3/2014 |
| WO | 2014035471 A1 | 3/2014 |

SYSTEM AND METHOD FOR IMPROVED FLUID FLOW CONTROL WITHIN A FLUID CIRCUIT CASSETTE

CROSS-REFERENCE TO RELATED APPLICATIONS

This application claims the benefit of U.S. Provisional Patent App. No. 62/297,549 filed Feb. 19, 2016, which is expressly incorporated herein by reference in its entirety.

FIELD OF THE DISCLOSURE

The present disclosure is directed to systems and methods for moving fluid through a fluid circuit. More particularly, the present disclosure relates to improved systems and methods to control fluid flow through a fluid circuit used in blood and blood component processing.

BACKGROUND

Whole blood may be collected from donors using manual collection procedures through blood drives, donor visits to blood centers or hospitals and the like. Blood may be collected by flowing it from the donor under the force of gravity and venous pressure into a collection container.

The collection container may be part of a larger pre-assembled arrangement of tubing and containers that may be used in further processing of the whole blood collected. Specifically, the whole blood may be first collected in what is called a primary collection container that also contains an anticoagulant, such as but not limited to a solution of sodium citrate, phosphate and dextrose (CPD).

After initial collection, the collected whole blood may be transported to another facility or location, sometimes called a "back lab," for further processing. This processing may entail loading the primary collection container and associated tubing and satellite containers onto a blood separation device to separate the whole blood into plasma and concentrated red cells. The separated components may then be expressed into one or more of the satellite containers and the red cells combined with an additive or preservative solution pre-filled in one of the satellite containers. The collected components may be even further processed, stored for future use, or immediately used, depending on different objectives.

SUMMARY

According to an exemplary embodiment, the present disclosure is directed to a fluid processing system for controlling fluid flow, comprising a cassette having a defined passageway on a first side, wherein the first side includes flexible sheeting disposed over the passageway. A durable processing device is configured to engage the first side of the cassette, and the durable processing device comprises a valve actuator configured to engage the flexible sheeting at a valve location along the defined passageway. A first pump is configured to draw fluid away from the valve location along the defined passageway, and the first pump is disposed downstream of the valve location. A second pump is configured to pump fluid towards the valve location along the defined passageway, and the second pump is disposed upstream of the valve location. The first and second pumps are configured to operate in concert, and are configured to provide sufficient pressure to prevent collapsing of the flexible sheeting against the passageway during operation.

According to an exemplary embodiment, the present disclosure is directed to a fluid processing system for controlling fluid flow, comprising a cassette having a defined passageway on a first side, wherein the first side includes flexible sheeting disposed over the passageway. A durable processing device is engaged with the first side of the cassette, and the durable processing device comprises a valve actuator configured to engage the flexible sheeting at a valve location along the defined passageway. A first pump is coupled to the durable processing device, and the first pump is disposed downstream of the valve location and is configured to draw fluid away from the valve location along the defined passageway. A fluid supply container is in communication with the defined passageway and disposed at a height above the cassette to provide positive hydrostatic pressure at the valve location when the first pump draws fluid away from the valve location. The first pump and fluid container are configured to provide sufficient pressure to prevent collapsing of the flexible sheeting against the passageway during operation.

According to an exemplary embodiment, the present disclosure is directed to a method for transferring fluid through a fluid flow path, comprising providing a cassette having a defined passageway with a valve location on a first side, wherein the first side includes flexible sheeting disposed over the passageway. The method also comprises providing a durable processing device configured to engage the first side of the cassette and comprising a valve actuator configured to engage the flexible sheeting at the valve location along the defined passageway. The method also comprises providing a first and second pump configured to be operated in concert, wherein the first pump is disposed downstream of the valve location and is configured to draw fluid away from the valve location along the defined passageway, and wherein the second pump is disposed upstream of the valve location and is configured to pump fluid towards the valve location along the defined passageway. The method also comprises providing a fluid supply container in communication with the defined passageway and disposed at a height above the cassette to provide hydrostatic pressure at the valve location when the pumps operate in concert, wherein the pumps and fluid container are configured to provide sufficient pressure to prevent collapsing of the flexible sheeting against the passageway during operation.

BRIEF DESCRIPTION OF THE DRAWINGS

Features, aspects, and advantages of the present embodiments will become apparent from the following description, appended claims, and the accompanying exemplary embodiments shown in the drawings, which are briefly described below.

DETAILED DESCRIPTION

There are several aspects of the present subject matter which may be embodied separately or together in the devices and systems described and claimed below. These aspects may be employed alone or in combination with other aspects of the subject matter described herein, and the description of these aspects together is not intended to preclude the use of these aspects separately or the claiming of such aspects separately or in different combinations as set forth in the claims appended hereto.

Some embodiments may allow for the operation of cassette valves without the use of a vacuum.

Some embodiments may allow for pressure to be maintained at a valve without the use of a vacuum.

There have been continuing efforts to automate the apparatus and systems used in the post-collection processing of whole blood, and an automated blood component separator for such post-collection processing may be employed. One class of such automated separators employs relatively rotating surfaces, at least one of which carries a porous membrane. An example of such a membrane separator is disclosed in PCT Patent Application Publication No. WO 2014/039086 A1, which is incorporated by reference in its entirety, although any suitable membrane separator may be used. Another class employs a centrifuge that utilizes centrifugal separation principles. An exemplary centrifugal separator is disclosed in U.S. Pat. No. 5,868,696, which is incorporated by reference in its entirety, although any suitable centrifugal separator may be used.

Both membrane separation and centrifugal separation systems may involve a durable processing system or device used in combination with a disposable processing set or circuit. The durable processing system may include a pump assembly that interacts with one or more of the components of the disposable circuit to draw blood or other bodily fluid from a blood source and move the blood or bodily fluid to another location within the disposable circuit by moving fluid through a fluid flow path.

One component of the disposable circuit that interacts with the pump assembly may be a molded plastic piece commonly referred to as a cassette. As used herein, the term "cassette" refers to a component of a fluid processing system that includes one or more defined fluid passageways. The cassette may be secured to a cassette holder or cassette station of the durable equipment, with a flexible sheeting or diaphragm of the cassette facing the durable equipment. The cassette holder or cassette station may include a number of valve actuators that selectively press against the flexible diaphragm/sheeting for opening and closing valve stations of the cassette, thereby controlling which of the fluid passageways are connected to each other and directing the fluid between any of a number of sources and destinations. Flexible tubing loops connected to select edges of the cassette may be received within peristaltic pump stations having rollers that press against the loops and rotate to move fluid through the cassette (and through the other components of the disposable circuit). An exemplary cassette is disclosed in U.S. Pat. No. 5,868,696, which is incorporated by reference herein in its entirety, although any suitable cassette may be used.

Figure 1:
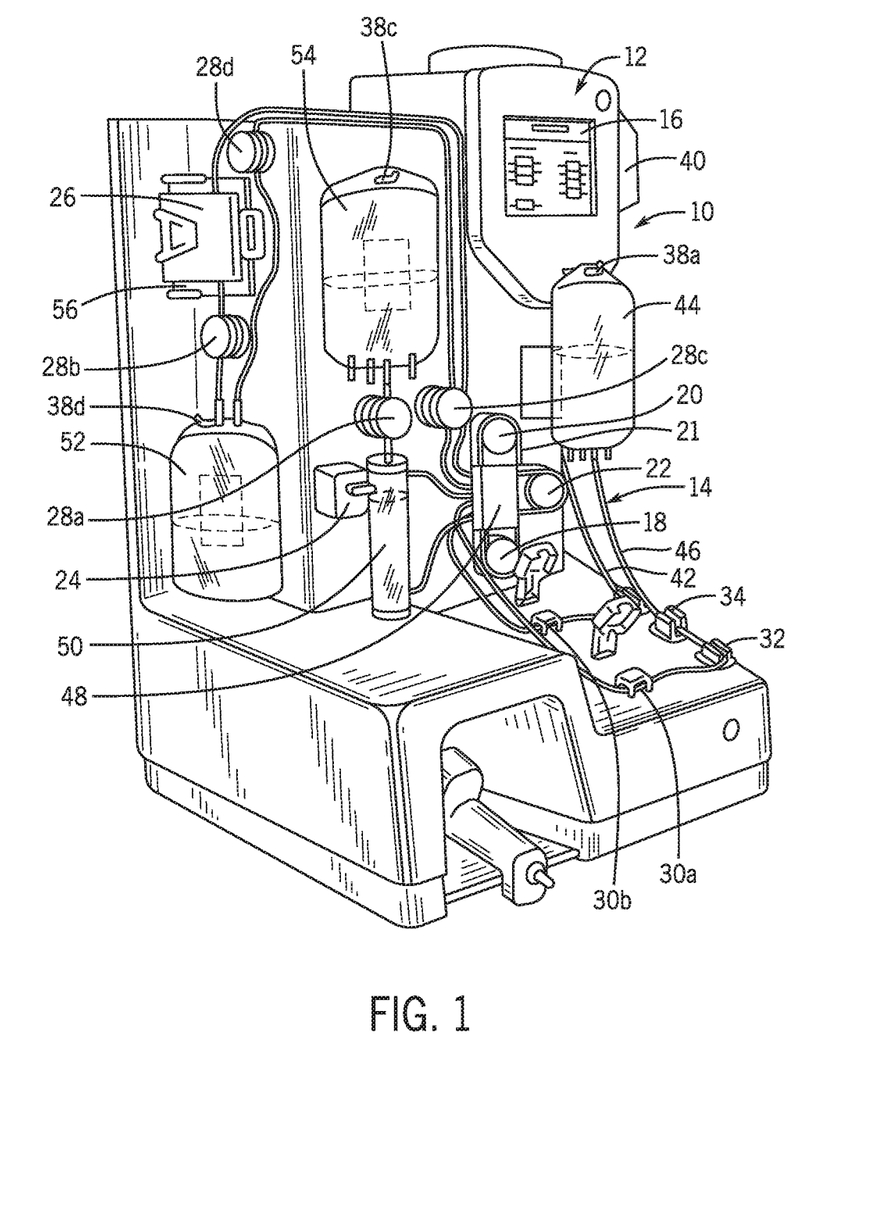
FIG. 1 is a perspective view of a blood processing system employing a durable processing device and a disposable fluid flow circuit, according to an exemplary embodiment.

FIG. 1 depicts a blood processing system, generally at 10, which includes a durable reusable processing device 12 and a disposable fluid flow circuit 14 for processing collected whole blood. The illustrated blood processing device 12 includes associated pumps, valves, sensors, displays and other apparatus for configuring and controlling flow of blood and additive solution through the disposable circuit. The device and the processing may be directed by an internal controller that includes a programmable microprocessor automatically controlling the operation of the pumps, valves, sensors, etc.

The processing device 10 may include a user input and output touch screen 16, a pump station including a whole blood pump 18, an RBC pump 20 and an additive solution pump 22, blood separator mounting station and drive unit 24, leukocyte filter housing 26, tubing clamps 28a-28d, sterile connection or docking devices 30a, 30b, one or more tubing clamps 32, and hematocrit sensor 34. The processing device may also include hangers 38a-d, each associated with a weight scale, for suspending the various containers of the disposable fluid circuit.

The fluid flow circuit 14 may include an additive solution container 40 and associated fluid flow tubing 42 for withdrawing the additive solution, a whole blood container 44 and associated fluid flow tubing 46 for withdrawal of collected whole blood from the container, and a processing module that includes pump cassette 48, separator 50 (e.g., spinning membrane separator, separation chamber placed within a centrifuge), red blood cell (RBC) container 52, plasma container 54, leukoreduction filter 56 (as shown, located within housing 26) and associated connecting tubing. The pump cassette 48 may route the fluid flow through tubing loops 21 that extend from the cassette, and each loop may be uniquely positioned to engage a particular one of the pumps 18, 20, and 22. The tubing may extend through the cassette or the cassette may have pre-formed fluid flow paths that direct the fluid flow.

Figure 2:
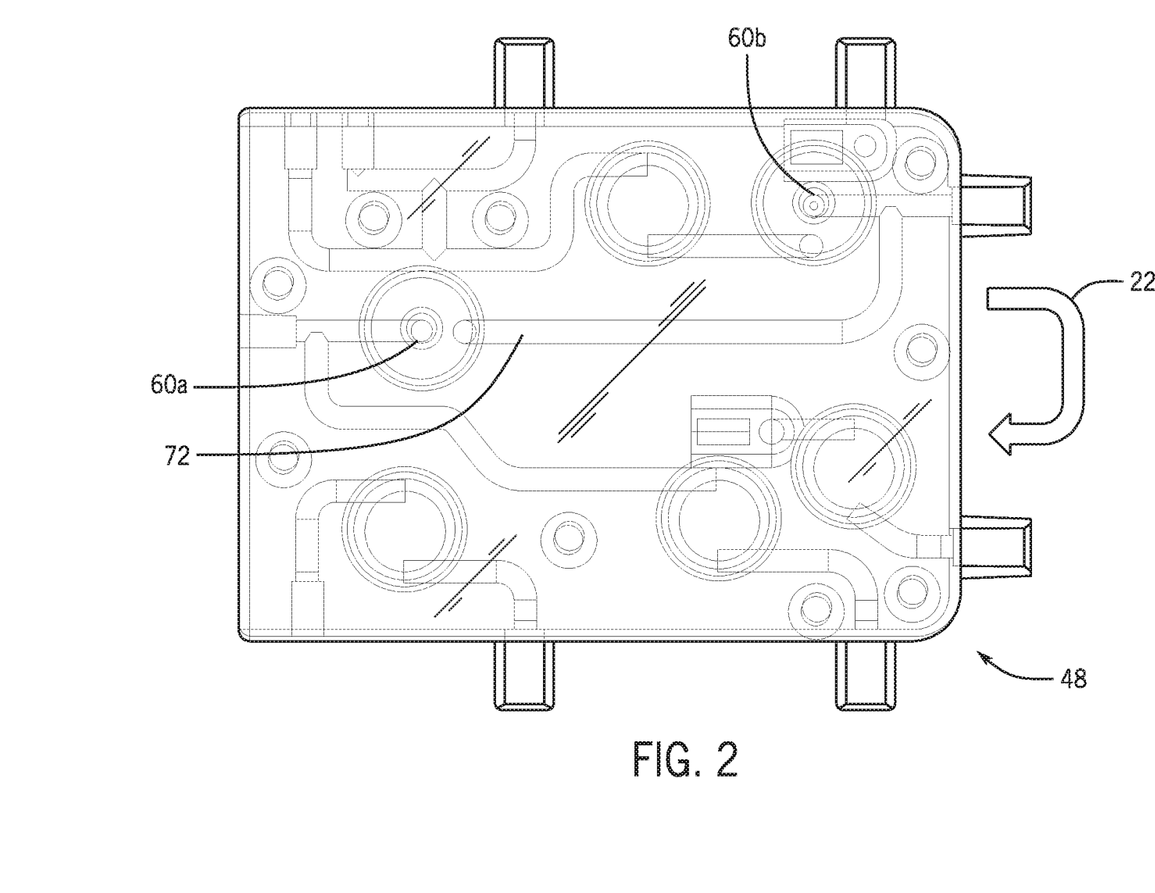
FIG. 2 is a top view of a pump cassette showing inner architecture, according to an exemplary embodiment.

Turning to FIG. 2, a detailed view of the pump cassette 48 from the top is shown. Any cover that the cassette 48 may have is shown as removed to depict the inner architecture. The embodiment of FIG. 2 shows two valve stations 60a and 60b, which allow fluid to pass through a fluid passageway 72 when in an open state and prevent fluid from passing in a closed state. The cassette station of the durable processing device 12 upon which the cassette 48 is mounted may be equipped with valve actuators 61 (FIG. 3) that engage the flexible sheeting 71 of the cassette 48 to control open and closed states.

Figure 3:
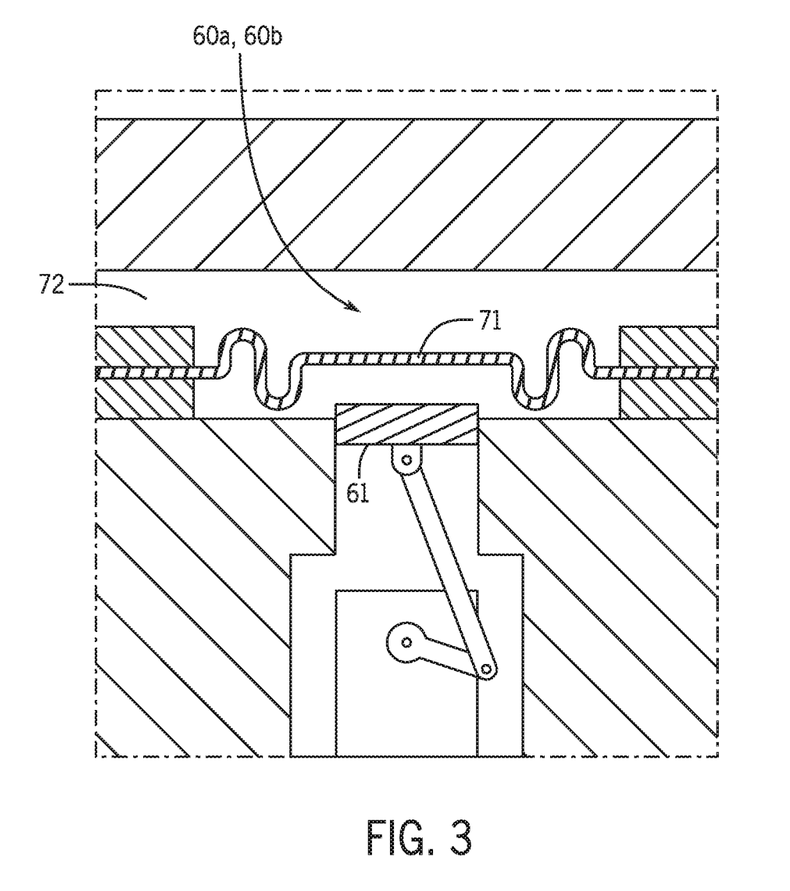
FIG. 3 is a side cross-sectional view of a valve station in an open state, according to an exemplary embodiment.
Figure 4:
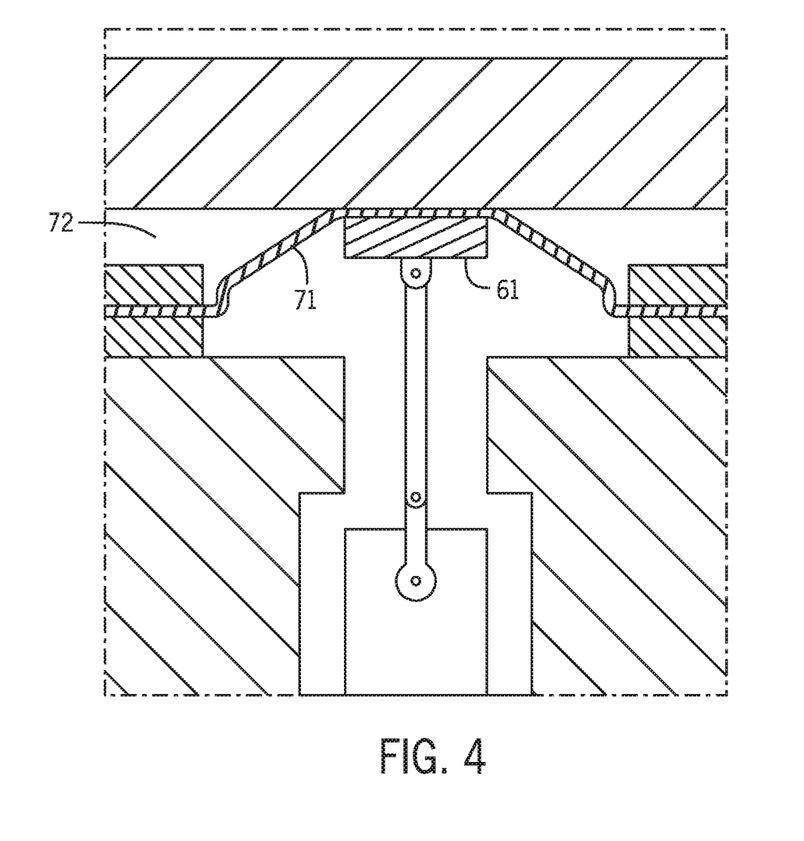
FIG. 4 is a side cross-sectional view of a valve station in a closed state, according to an exemplary embodiment.

FIG. 3 shows a side cross-section view of a valve station 60a or 60b in an open state. In this open state, valve actuator 61 is not engaged with flexible sheeting 71, and fluid is free to flow along a pressure gradient that can be created and controlled by the pumps 18, 20, 22 (FIG. 1). FIG. 4 shows a side cross-section view of a valve station 60a or 60b in a closed state. In this closed state, valve actuator 61 is fully engaged with flexible sheeting 71, whereby such engagement obstructs fluid flow within the fluid passageway 72.

Figure 5A:
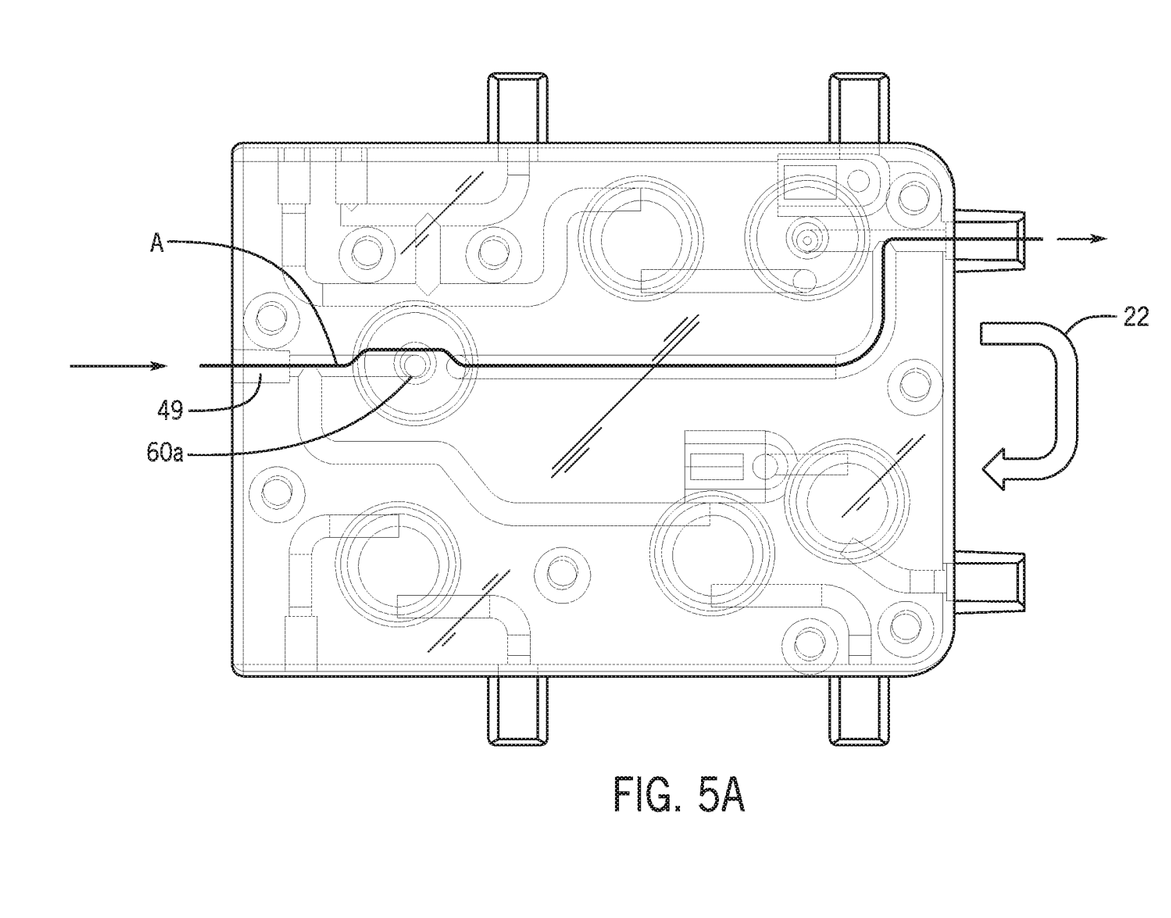
FIG. 5A is a schematic view of a fluid flow path within a cassette in communication with a pump disposed downstream of a valve station, according to an exemplary embodiment.
Figure 5B:
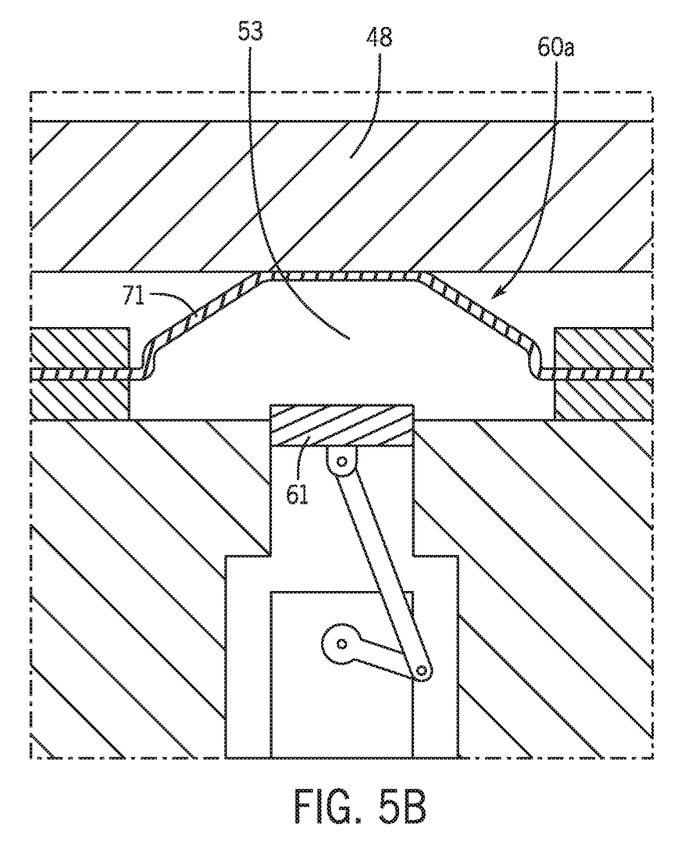
FIG. 5B is a cross-sectional view of a valve station showing cassette sheeting collapsing against the cassette, according to an exemplary embodiment.

FIG. 5A illustrates a mechanism used to help prevent obstructions within certain fluid flow paths. For example, fluid flow path A is shown extending from port 49 to pump 22. As pump 22 draws fluid away from valve station 60a towards pump 22, pressure at the valve station 60a drops, which could lead to sheeting 71 at valve station 60a collapsing against the cassette 48 before fluid upstream proximal to port 49 can flow in to compensate for the pressure differential. FIG. 5B illustrates an example of when the sheeting 71 at valve station 60a collapses against cassette 48, leading to obstruction of flow. A solution to the obstruction of flow as described above has been to implement a vacuum, as the fluid flows, on the opposite side of the sheeting 71 generally at area 53 between the sheeting 71 and actuator 61 in the embodiment of FIG. 5B. An example of vacuum implementation is described in greater detail in U.S. Pat. No. 7,789,245, the contents of which are incorporated by reference herein in its entirety.

Figure 6A:
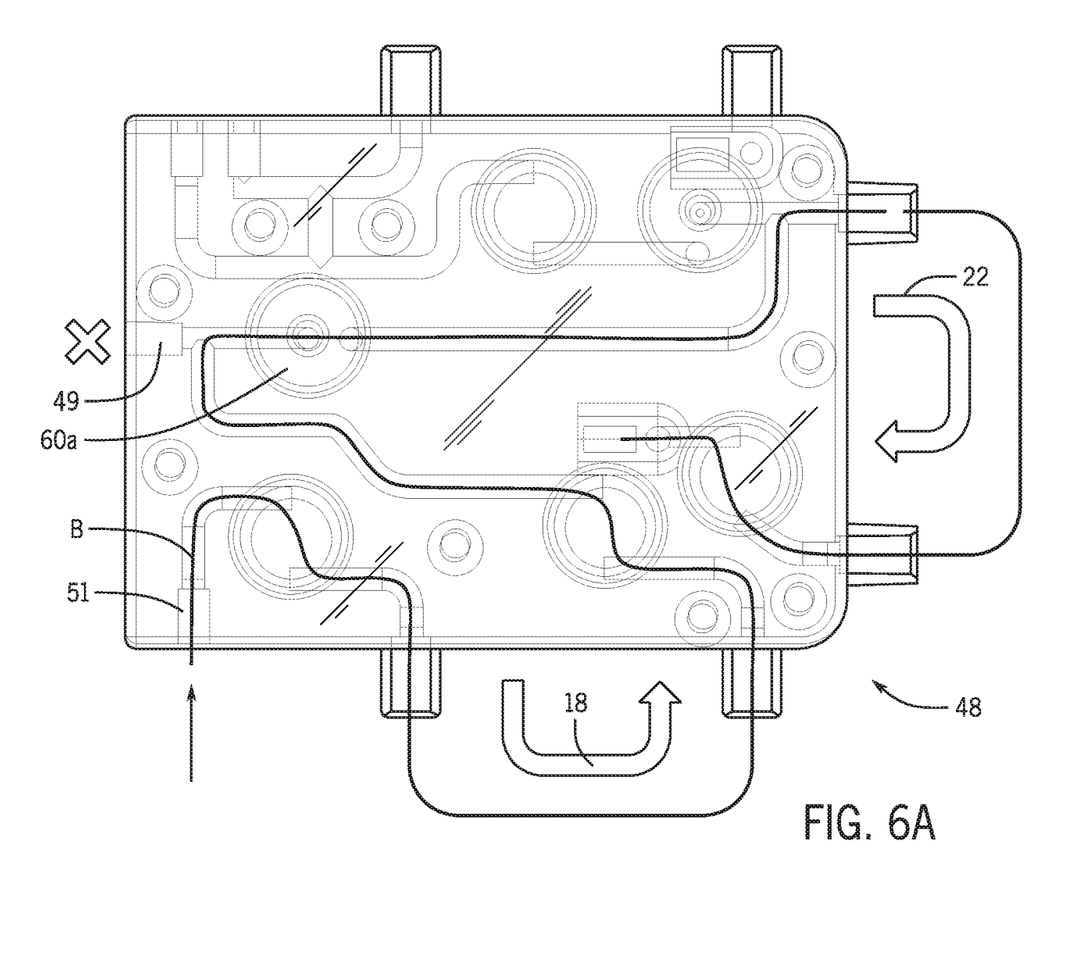
FIG. 6A is a schematic view of a fluid flow path within a cassette in communication with pumps disposed upstream and downstream of a valve station, according to an exemplary embodiment.

In lieu of or in conjunction with implementing a vacuum, the collapsing of sheeting 71 against cassette 48 may be prevented by providing positive pressure upstream of the valve station to compensate for the pressure drop distal to the valve station. For example, FIG. 6A shows the use of an alternate fluid flow path B from port 51 to pump 22. In addition to a first pump 22 located downstream of valve station 60a drawing fluid away from valve station 60a, fluid flow path B may incorporate a second pump 18 located upstream of valve station 60a to actively pump fluid towards station 60a to provide positive pressure upstream of valve station 60a and prevent collapsing of sheeting 71 against the cassette 48. The second pump 18 may engage one of the tubing loops 21 (FIG. 1) extending from the cassette 48 and may pump fluid in concert with the first pump 22. As used herein, the phrase "in concert" may refer to simultaneous and/or near simultaneous operation. In addition, it may refer to the operation and/or configuration of two or more elements such that each element, alone or together in combination, contributes to a particular objective or function. For example, the pumps may operate at the same time or substantially at the same time and may function alone or together to displace fluid within a fluid circuit and/or regulate a pressure within a designated valve station. According to various exemplary embodiments, the rate of the pumps may be the same, substantially the same, different, or may vary over time and/or relative to each other. According to exemplary embodiments, various factors may be considered in order to reach the appropriate pressure at valve station 60a and prevent collapsing of the sheeting 71, including, for example, pump rates, valve station location and/or sizing, fluid flow path configuration, pump location, tubing diameter, cassette and/or sheeting materials, use or non-use of vacuums, fluid characteristics, head height of fluid containers, etc.

Figure 6B:
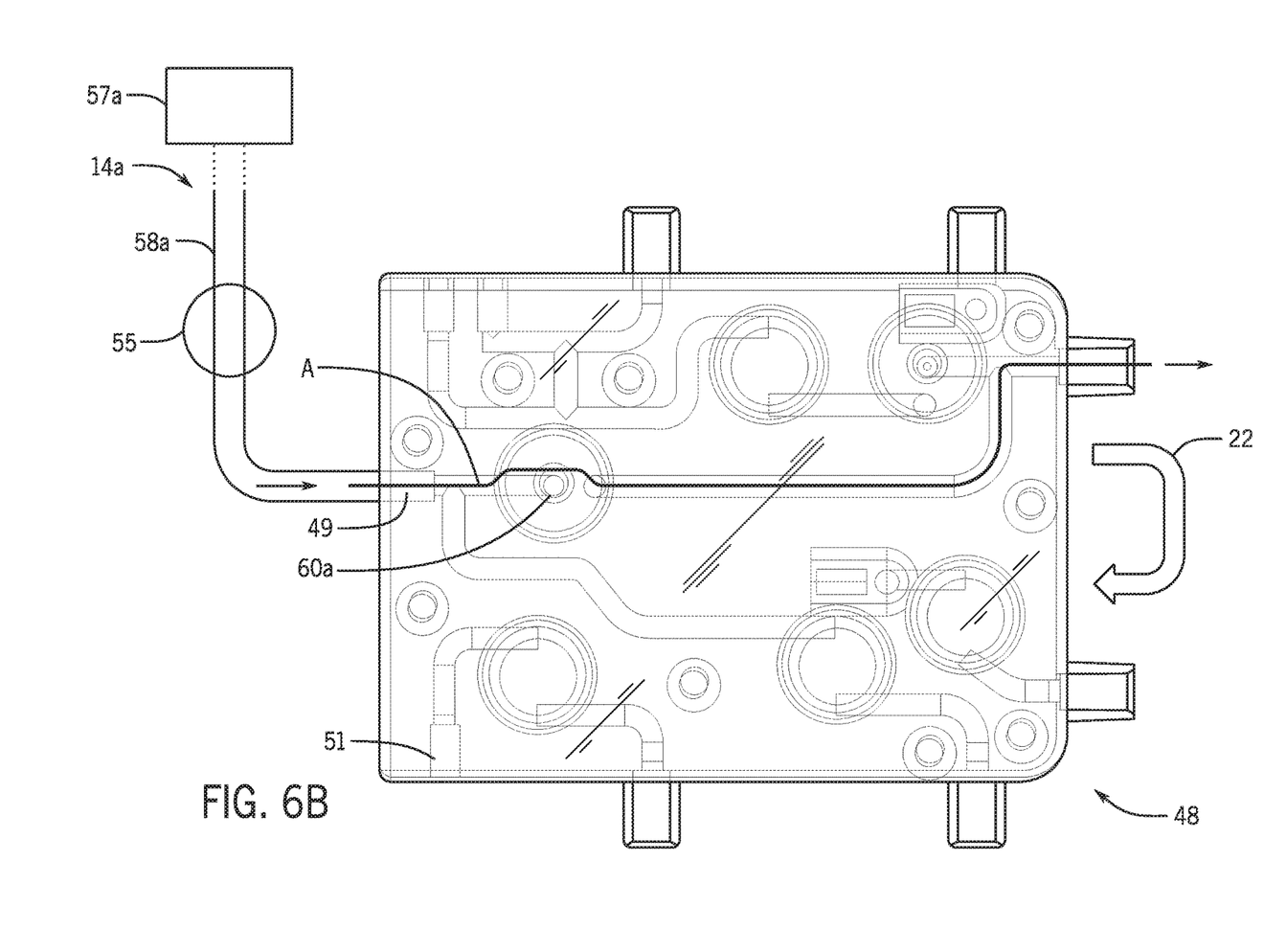
FIG. 6B is a schematic view of a fluid flow path within a cassette in communication with pumps disposed upstream and downstream of a valve station, according to an exemplary embodiment.

According to exemplary embodiments, the second pump that actively pumps fluid towards the valve station may be disposed in any suitable location upstream of the valve station, including upstream of the cassette station. For example, FIG. 6B shows fluid circuit 14a, which includes tubing 58a that extends from a component of fluid circuit 14a, e.g., a fluid source 57a, to port 49 of cassette 48. Pump 55 provides positive pressure to fluid circuit 14a by engaging tubing 58a at a location upstream of valve station 60a. Pump 55 may be configured to engage tubing 58a at any suitable location along the fluid circuit 14a upstream of valve station 60a. Pump 55 may be a manual or automated pump and may be an integral part of the processing device 10 or a stand-alone pump used to provide positive pressure upstream of valve station 60a.

Figure 7:
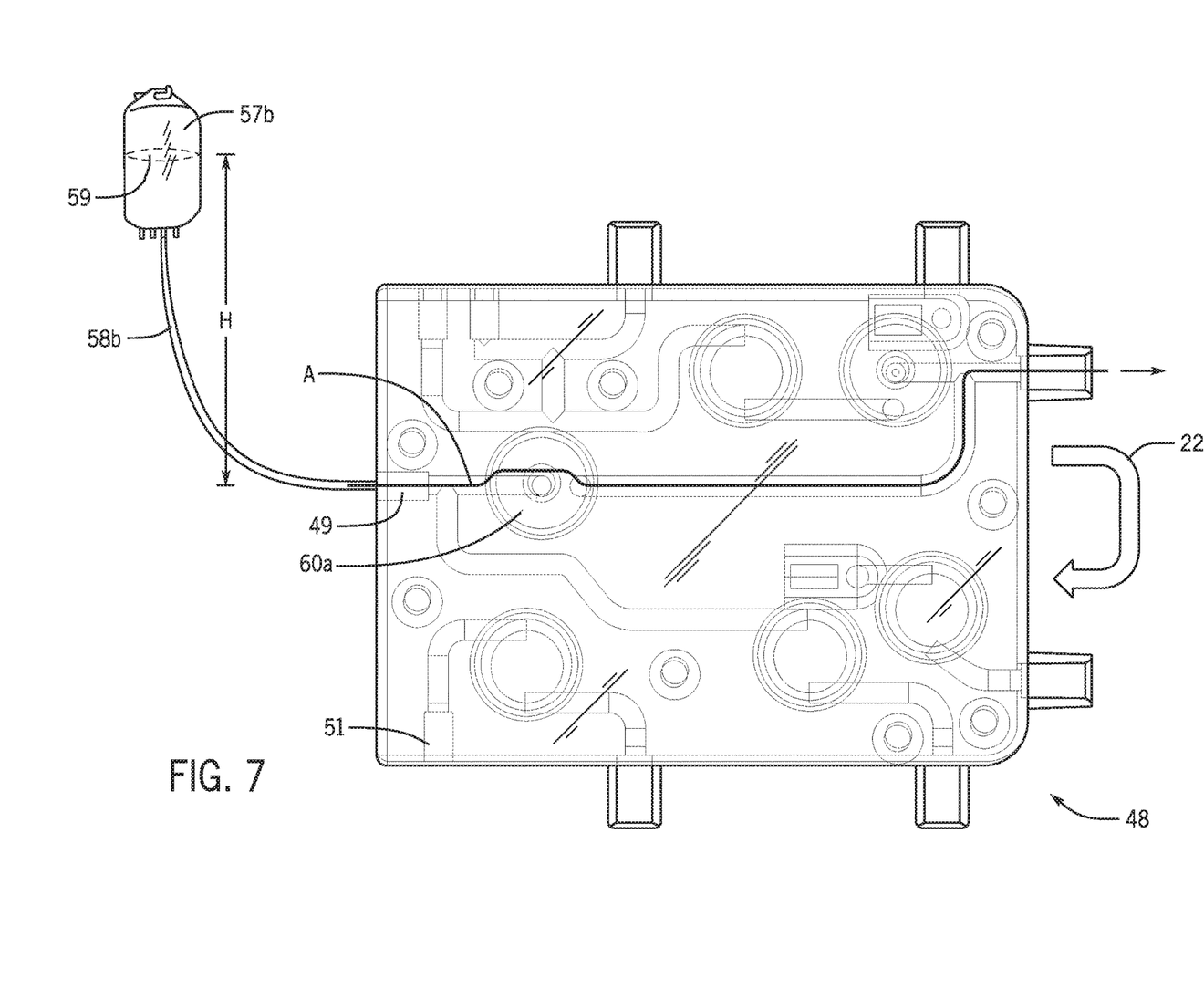
FIG. 7 is a schematic view of a fluid-filled container in communication with a flow path within a cassette in communication with a pump disposed downstream of a valve station, according to an exemplary embodiment.

According to other exemplary embodiments, positive pressure upstream of a valve station may be achieved by utilizing hydrostatic pressure in lieu of or in combination with a vacuum and/or one or more pumps. Turning to FIG. 7, a fluid container 57b holding a volume of fluid is connected by way of tubing 58b to a port 49 of cassette 48. Fluid container 57b may be arranged such that the top surface 59 of the fluid in container 57b is at a height H relative to the height of valve station 60a in order to provide suitable hydrostatic pressure conducive to preventing collapse of the sheeting against the cassette. The height H may be varied depending on a number of factors including, for example, the number and/or location of one or more pumps, pump speed, fluid composition, etc. According to an exemplary embodiment based on a study conducted to evaluate suitable hydrostatic pressure levels, when pump 22 was configured to pump fluid at a rate within the range of 2 ml/min to 20 ml/min, collapse of the sheeting against the cassette 48 was prevented when the fluid-filled container 57b was positioned at a height H that was above 0.10 meters, and preferably at a H of approximately 0.15 meters. Utilizing the equation for hydrostatic pressure P=pgh, where P is hydrostatic pressure (Pa), g is the atmospheric acceleration (m/s$^2$), p is density of the fluid, and h is the height (meters) at which the fluid is held relative to the valve 60a, the hydrostatic pressure providing positive pressure at the valve station 60a may be calculated. In an embodiment in which the fluid container 57b is held by the processing device 12 at a height H of 0.15 meters relative to the valve station 60a and provided that the density of water p is approximately 1000 kg/m$^3$ (when fluid providing hydrostatic pressure is water or primarily water) and gravity is approximately 9.8 m/s$^2$, the hydrostatic pressure provided by the fluid container 57b can be calculated to be approximately 1470 Pa. In an embodiment in which the fluid container 57b is held by the processing device 12 at a minimum height H of 0.10 meters relative to the valve station 60a, the same equation P=pgh can be used to calculate that the minimum hydrostatic pressure for maintaining positive pressure at valve station 60a is approximately 980 Pa. Depending on the density p of the fluid in container 57 and the surrounding gravity g, the height H and/or the hydrostatic pressure P required to prevent collapse of the cassette sheeting may vary.

Fluid from container 57 used to provide hydrostatic pressure may include solutions and/or liquids suitable for blood processing procedures. Examples of such fluids include, but are not limited to, blood or blood components, anticoagulant, additive and/or preservative solution, saline, and/or any other fluid suitable for routing through the cassette 48 of the processing device 10.

Figure 8:
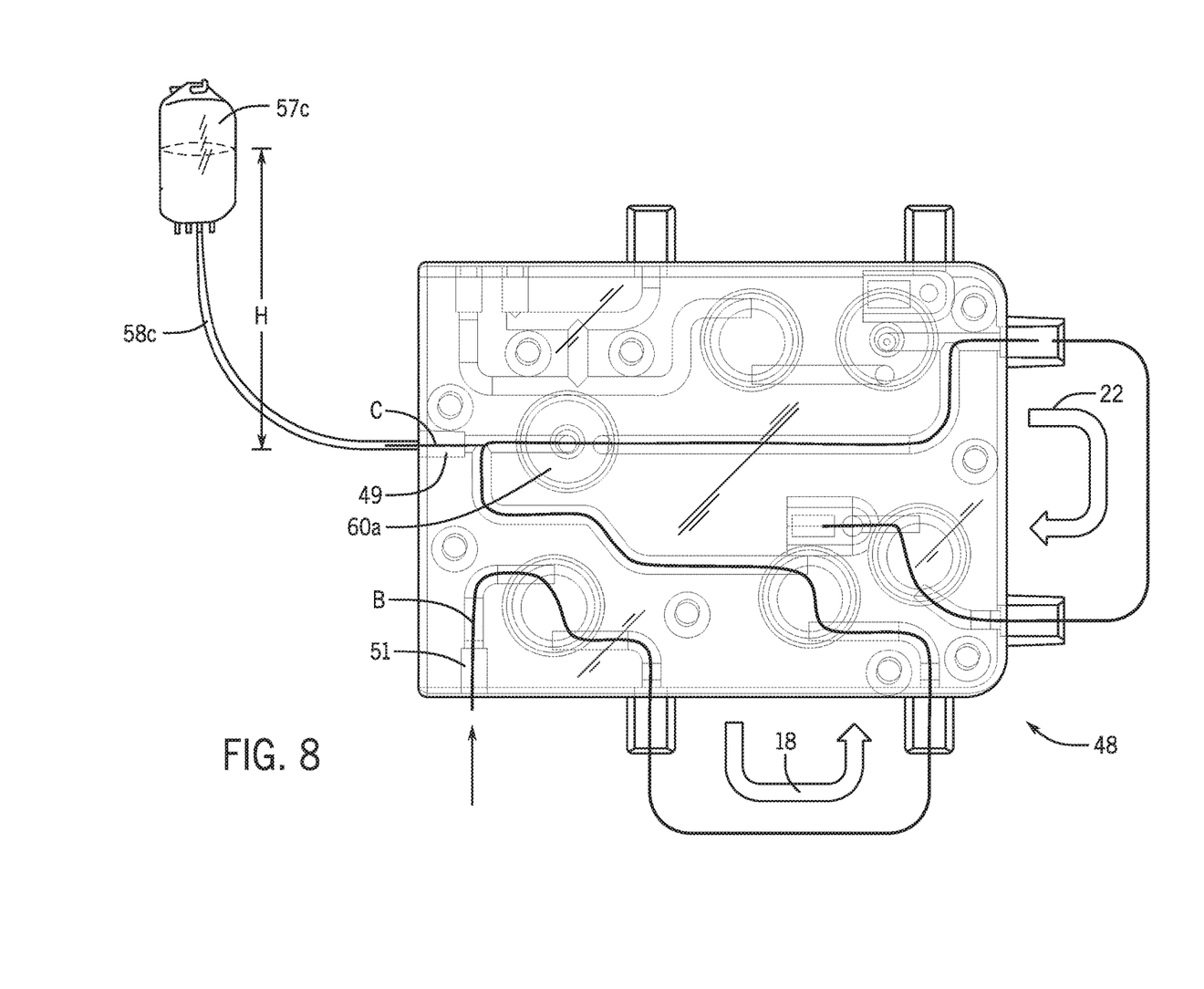
FIG. 8 is a schematic view of a fluid flow path within a cassette in communication with pumps disposed upstream and downstream of a valve station and in communication with a fluid-filled container, according to an exemplary embodiment.

According to other exemplary embodiments, positive pressure upstream of a valve station may be achieved by utilizing hydrostatic pressure in concert with a first pump located downstream of a valve station and a second pump located upstream of the valve station. For example, FIG. 8 shows fluid flow path B from port 51 to pump 22 and fluid flow path C from port 49 to pump 22 merging at or near the valve station 60a and together flowing downstream to pump 22. The first pump 22 located downstream of valve station 60a may draw fluid away from valve station 60a, and a second pump 18 located upstream of valve station 60a along flow path B may be incorporated to actively pump fluid towards station 60*a* to provide positive pressure upstream of valve station 60*a* and prevent collapsing of the sheeting against the cassette 48. A fluid container 57*c* holding a volume of fluid may be connected by tubing 58*c* to port 49 and provide a fluid source for fluid flow path C flowing into the cassette 48 from port 49. Fluid container 57*c* may be arranged such that the top surface 59 of the fluid in container 57*c* is at a height H relative to the height of valve station 60*a* in order to provide suitable hydrostatic pressure conducive to preventing collapse of the sheeting against the cassette. The height H may be varied depending on a number of factors including, for example, the number and/or location of one or more pumps, pump speed, fluid composition, etc. Likewise, the pump rates of the first pump 22 and the second pump 18 may be the same, substantially the same, different, or may vary over time and/or relative to each other. In an embodiment in which both hydrostatic pressure from fluid container 57*c* and fluid pressure from upstream pump 18 contribute to the resulting total positive pressure at valve station 60*a*, head height H and pump rates can be adjusted so that the total positive pressure at valve station 60*a* is within the desired range. According to exemplary embodiments, various factors may be considered in order to reach the appropriate pressure at valve station 60*a* and prevent collapsing of the sheeting 71, including, for example, pump rates, valve station location and/or sizing, fluid flow path configuration, pump location, tubing diameter, cassette and/or sheeting materials, use or non-use of vacuums, fluid characteristics, head height of fluid containers, etc.

The embodiments disclosed herein are for the purpose of providing a description of the present subject matter, and it is understood that the subject matter may be embodied in various other forms and combinations not shown in detail. Therefore, specific embodiments and features disclosed herein are not to be interpreted as limiting the subject matter as defined in the accompanying claims.

The invention claimed is:

1. A fluid processing system for controlling fluid flow, comprising:
   a cassette comprising a defined passageway on a first side, wherein the first side includes flexible sheeting disposed over the passageway; and
   a durable processing device configured to engage the first side of the cassette, the durable processing device comprising
      a valve actuator configured to engage the flexible sheeting at a valve location along the defined passageway,
      a first pump configured to draw fluid away from the valve location along the defined passageway, wherein the first pump is disposed downstream of the valve location,
      a second pump configured to pump fluid towards the valve location along the defined passageway, wherein the second pump is disposed upstream of the valve location, and
      a controller configured to control the first and second pumps to operate in concert so as to provide sufficient pressure to prevent collapsing of the flexible sheeting against the passageway during operation.

2. The fluid processing system of claim 1, wherein a vacuum for controlling fluid flow is not implemented between the flexible sheeting and the durable processing device.

3. The fluid processing system of claim 1, wherein the controller is configured to control the first and second pumps so as to have approximately the same pump rates.

4. The fluid processing system of claim 1, wherein the second pump is engaged with a tubing loop extending from the cassette.

5. The fluid processing system of claim 1, wherein the second pump is engaged with a tubing length that is in communication with the defined passageway at one end of the tubing length.

6. The fluid processing system of claim 5, wherein the second pump is a manual stand-alone pump.

7. The fluid processing system of claim 5, wherein the second pump is an automated pump integral to the processing device.

8. A fluid processing system for controlling fluid flow, comprising:
   a cassette comprising a defined passageway on a first side, wherein the first side includes flexible sheeting disposed over the passageway;
   a durable processing device engaged with the first side of the cassette, the durable processing device comprising a valve actuator configured to engage the flexible sheeting at a valve location along the defined passageway;
   a first pump coupled to the durable processing device, wherein the first pump is disposed downstream of the valve location and is configured to draw fluid away from the valve location along the defined passageway; and
   a fluid supply container in communication with the defined passageway and disposed at a height above the cassette to provide positive hydrostatic pressure at the valve location when the first pump draws fluid away from the valve location, wherein the first pump and fluid container are configured to provide sufficient pressure to prevent collapsing of the flexible sheeting against the passageway during operation.

9. The fluid processing system of claim 8, wherein a vacuum for controlling fluid flow is not implemented between the flexible sheeting and the durable processing device.

10. The fluid processing system of claim 8, wherein the pump is configured to pump fluid at a rate in the range of 2 ml/min to 20 ml/min.

11. The fluid processing system of claim 8, wherein the hydrostatic pressure provided by the fluid supply container is at least 980 Pa.

12. The fluid processing system of claim 8, wherein the fluid supply container is positioned at a height of at least 0.10 meters above the valve location.

13. The fluid processing system of claim 8, wherein the fluid supply container comprises at least one of blood, blood components, anticoagulant, additive solution, preservative solution, and saline.

14. A method for transferring fluid through a fluid flow path, comprising:
   providing a cassette comprising a defined passageway with a valve location on a first side, wherein the first side includes flexible sheeting disposed over the passageway;
   providing a durable processing device configured to engage the first side of the cassette and comprising a valve actuator configured to engage the flexible sheeting at the valve location along the defined passageway;
   providing a first and second pump configured to be operated in concert, wherein the first pump is disposed downstream of the valve location and is configured to draw fluid away from the valve location along the defined passageway, and wherein the second pump is disposed upstream of the valve location and is configured to pump fluid towards the valve location along the defined passageway; and providing a fluid supply container in communication with the defined passageway and disposed at a height above the cassette to provide hydrostatic pressure at the valve location when the pumps operate in concert, wherein the pumps and fluid container are configured to provide sufficient pressure to prevent collapsing of the flexible sheeting against the passageway during operation.

15. The method of claim 14, wherein a vacuum for controlling fluid flow is not provided between the flexible sheeting and the durable processing device.

16. The method of claim 14, wherein the second pump is configured to pump fluid in the range of 2 ml/min to 20 ml/min.

17. The method of claim 14, wherein the fluid supply container comprises at least one of blood, blood components, anticoagulant, additive solution, preservative solution, and saline.

18. The method of claim 14, wherein the second pump is positioned along the fluid flow path at a location upstream from the cassette.

19. The method of claim 18, wherein the second pump is a manual stand-alone pump.

20. The method of claim 18, wherein the second pump is an automated pump integral to the processing device.

* * * * *